United States Patent
Muramatsu et al.

(10) Patent No.: US 8,221,758 B2
(45) Date of Patent: Jul. 17, 2012

(54) ANTI-MIDKINE ANTIBODY FOR PREVENTING POST-LAPAROTOMY ADHESIONS

(75) Inventors: Takashi Muramatsu, Aichi (JP); Kazuhiko Inoh, Aichi (JP); Hisako Muramatsu, Aichi (JP); Shuhei Torii, Aichi (JP)

(73) Assignee: Cellmid Limited, Sydney (AU)

( * ) Notice: Subject to any disclaimer, the term of this patent is extended or adjusted under 35 U.S.C. 154(b) by 0 days.

(21) Appl. No.: 10/547,011

(22) PCT Filed: Mar. 5, 2004

(86) PCT No.: PCT/JP2004/002888
§ 371 (c)(1),
(2), (4) Date: Jan. 5, 2006

(87) PCT Pub. No.: WO2004/078210
PCT Pub. Date: Sep. 16, 2004

(65) Prior Publication Data
US 2006/0148738 A1    Jul. 6, 2006

(30) Foreign Application Priority Data
Mar. 6, 2003    (JP) ................................. 2003-108428

(51) Int. Cl.
*A61K 39/395*    (2006.01)

(52) U.S. Cl. ............... 424/145.1; 424/142.1; 424/141.1; 424/135.1; 424/133.1; 424/130.1

(58) Field of Classification Search ........................ None
See application file for complete search history.

(56) References Cited

U.S. PATENT DOCUMENTS
6,812,220 B2 * 11/2004 Jackson et al. .................. 514/54

FOREIGN PATENT DOCUMENTS
| JP | 62-155223 A | 6/1987 |
| JP | 2002-142778 A | 5/2002 |
| WO | WO 99/03493 A1 | 1/1999 |
| WO | WO 00/10608 A1 | 3/2000 |

OTHER PUBLICATIONS

Takei et al (J. Biol. Chem 277(26): 23800-23806, 2002).*
Takei et al. J. Biol. Chem. 277(26): 23800-23806, 2002.*
Horiba et al. The Journal of Clinical Investigation, 2000, 105:489-495.*
Vural, Birol (1999) "The role of neutrophils in the formation of peritoneal adhesions" *Human Reproduction* 14(1):49-54.

* cited by examiner

*Primary Examiner* — Sharon Wen
(74) *Attorney, Agent, or Firm* — Morrison & Foerster LLP

(57) ABSTRACT

The present inventors discovered that oligonucleotides which suppress midkine expression and antibodies which suppress midkine activity can be used to prevent post-surgical intraperitoneal adhesions.

7 Claims, 4 Drawing Sheets

ANTI-MIDKINE ANTIBODY FOR PREVENTING POST-LAPAROTOMY ADHESIONS

This application is a National Stage Application of International Application Number PCT/JP2004/002888, filed Mar. 5, 2004; which claims priority to Japanese Application No. 2003-108428, filed Mar. 6, 2003.

TECHNICAL FIELD

The present invention relates to prevention of post-laparotomy adhesions.

BACKGROUND ART

Although the incidence rate of post-laparotomy adhesion varies from report to report, adhesions are reportedly formed in 90% or more of major laparotomy cases and in 55-100% of patients who undergo gynecologic laparotomy. Mechanical stimuli produced by laparotomy operations may cause inflammation in intraperitoneal organs, and consequently, cause adhesions between the intraperitoneal organs or between the intraperitoneal organs and the peritoneal wall. This may cause intestinal passage obstruction or constriction and lead to adhesive ileus. Even if adhesive ileus does not develop, chronic abdominal pain and female infertility can result. Furthermore, such adhesions make it very difficult to perform future laparotomies. It is not uncommon for adhesive ileus to is often develope decades after a laparotomy, and a second laparotomy followed by adhesiotomy is often needed for the treatment. However, this operation may result in further adhesions. The formation of post-laparotomy adhesions is a serious problem and has been neglected as it is considered to be an inevitable side effect. Recently, an absorbent membrane (Seprafilm; Kaken Pharmaceutical Co., Ltd.) which is placed in the peritoneal cavity to prevent adhesions was developed. However, the membrane is only effective in preventing adhesions in regions that are separated by it, and cannot exert its adhesion prevention effect throughout the whole peritoneal cavity. New technologies that prevent post-surgical adhesions in the peritoneal cavity are thus desired.

DISCLOSURE OF THE INVENTION

An objective of the present study is to provide novel pharmaceutical agents for preventing post-surgical intraperitoneal adhesions.

The present inventors systematically investigated whether there are differences in the degree of adhesion between mice having different genetic backgrounds. Surprisingly, intraperitoneal adhesions in wounds made in the peritoneal cavity were significantly reduced in midkine gene-knockout mice (midkine (−/−) mice) as compared with wild-type mice. Further, although the formation of adhesions was suppressed in the midkine (−/−) mice, the process was resumed upon supplying midkine to the mice. Migration of macrophages and neutrophils to the omentum was suppressed in the midkine (−/−) mice. The present inventors revealed from these findings that midkine plays a critical role in intraperitoneal adhesions and can thus be a molecular target for adhesion suppression.

It has been reported that midkine is a growth factor that enhances cell growth, migration, and survival (Muramatsu, T. Wiley Encyclopedia Mol, 2086-2088, 2002;Muramatsu, T., J. Biochem., 132, 359-371, 2002), and that it participates in inflammatory responses by promoting the migration of neutrophils and macrophages to inflammatory sites (Takada, T. et al., J. Biochem. 122, 453-458, 1997;Horiba, M. et al., J. Clin. Invest. 105, 489-495, 2000). The above-described findings revealed that midkine is also involved in adhesion formation.

Specifically, the present invention relates to adhesion prevention by inhibiting midkine synthesis or function.

The adhesion frequency following peritoneal wall injury in midkine gene knockout mice (Nakamura, E. et al., Genes Cells, 3, 811-822, 1998) was markedly lower when compared with the control wild-type mice (FIG. 1). Since the only difference between the knockout and the wild-type mice is the presence of the midkine gene, adhesions can be prevented or treated by suppressing the expression or activity of midkine.

Herein, the phrase "suppression of midkine gene expression" includes both transcriptional suppression and translational suppression. An oligonucleotide to be used to suppress midkine gene expression can be an RNA complementary to the transcript of the midkine gene or a DNA that encodes the RNA. An embodiment of such a compound may be an antisense oligonucleotide.

Previously developed antisense oligonucleotides which strongly suppress midkine expression (Takei, Y. et al., Cancer Res., 61 8486-8491, 2001;Japanese Patent Application Nos. 2002-142778, 2002-47135, and 2002-47136) may be used in the present invention. However, the present invention is not limited to these specific antisense oligonucleotides.

Herein, the term "oligonucleotide" encompasses nucleic acid moieties of naturally occurring oligomers, such as the DNA deoxyribonucleotide structure and the RNA ribonucleotide structure, and artificial analogs capable of binding to naturally occurring nucleic acids. The oligonucleotides of the present invention may be based on ribonucleotide monomers linked via phosphodiester bonds, or analogs linked via methylphosphonate bonds, phosphorothioate bonds, or other types of bonds. Such oligonucleotides may comprise monomer moieties having alterations in their basic or modified structures, but retaining the ability to bind naturally occurring DNA and RNA structures. Such oligonucleotides can be prepared by well-known methods, for example, a method using a commercially available device and reagents available through Perkin-Elmer/Applied Biosystems (Foster City, Calif.).

Oligonucleotides comprising phosphodiester bonds are particularly sensitive to nucleases in serum and cells. Thus, in a preferred embodiment of the present invention, the oligonucleotides are analogs linked via phosphorothioate bonds or methylphosphonate bonds and which have been revealed to be nuclease-resistant, and the like (Stein et al., Cancer Research 48; 2659, 1998). The method established by the present applicants (Japanese Patent Application No. 2002-47136) is also effective.

In another embodiment of the present invention, the antisense oligonucleotide is selected such that RNA molecules produced by transfecting target cells with an expression construct, hybridizes to midkine mRNA and inhibits its translation, thus inhibiting midkine synthesis.

Hybridizing the oligonucleotide with an mRNA target can inhibit the expression of the corresponding gene product via multiple mechanisms. In the state of "translation arrest", translation of the target mRNA into a protein is inhibited (Haeuptle et al.; Nucl. Acids. Res. 14: 1427, 1986). When the oligonucleotide is a phosphodiester DNA, phosphorothioate DNA, or the like, soon after a target RNA sequence hybridizes to the DNA oligomer, the target RNA sequence can be digested by intracellular RNase H (Walder & Walder, Proc. Natl. Acad. Sci. USA. 85: 5011, 1988). In another mechanism in the "translation arrest" state, certain types of oligonucleotides can form "triplexes", namely, triple helix structures, with a standard double-stranded genomic DNA comprising the gene of interest. Such helix structures have been shown to inhibit RNA polymerase-mediated transcription (Giovannangeli et al., Proc. Natl. Acad. Sci. USA. 90: 10013, 1993).

In another embodiment, the oligonucleotide that suppresses midkine gene expression is a dsRNA complementary to a transcript of the midkine gene, or a DNA encoding the RNA. The term "RNAi" refers to the phenomenon in which expressions of both the introduced foreign gene and the endogenous target gene are suppressed when a double-stranded RNA (hereinafter abbreviated as "dsRNA") comprising a sequence identical or similar to the target gene sequence is introduced into cells. When a dsRNA of about 40 to several hundred base pairs is introduced into cells, a helicase domain-containing RNase III-like nuclease called Dicer digests the dsRNA from its 3' end in the presence of ATP, and produces 21-23 base pair siRNAs (short interference RNAs). A specific protein then binds to the siRNA and forms a nuclease complex (RISC: RNA-induced silencing complex). The complex recognizes and binds to the same sequence as the siRNA, and the RNase III-like activity causes a cleavage of the target gene's mRNA in the middle of the siRNA. In a separate pathway, the antisense strand of the siRNA binds to mRNA and acts as a primer for RNA-dependent RNA polymerase (RsRP) to synthesize dsRNA. The dsRNA then serves as a new substrate for Dicer to generate new siRNAs, and the action is thereby amplified. Oligonucleotides of the siRNA method (McManus, M. T., Sharp P. A., Nature, 3, 737-747) can also be applied to the present invention.

The RNAi described above was originally discovered in nematodes (Fire, A. et al. Potent and specific genetic interference by double-stranded RNA in Caenorhabditis elegans. Nature 391, 806-811, (1998)). To date, RNAi has been observed not only in nematodes but also in various organisms such as plants, nemathelminthes, fruit fly, and protozoans (Fire, A. RNA-triggered gene silencing. Trends Genet. 15, 358-363 (1999); Sharp, P. A. RNA interference 2001. Genes Dev. 15, 485-490 (2001); Hammond, S. M., Caudy, A. A. & Hannon, G. J. Post-transcriptional gene silencing by double-stranded RNA. Nature Rev. Genet. 2, 110-1119 (2001); Zamore, P. D. RNA interference: listening to the sound of silence. Nat Struct Biol. 8, 746-750 (2001)). It has been confirmed that, in these organisms, the expression of target genes is indeed suppressed by introducing foreign dsRNAs. RNAi is being used as a technology to create knockouts.

At the time of RNAi discovery, it was believed that only dsRNAs of a certain length (40 nucleotides or longer) could produce a suppressive effect. However, Tuschl et al. at the Rockefeller University in the U.S. reported that introducing a single-chain dsRNA (siRNA) of about 21 base pairs into cells produces an RNAi effect without inducing PKR-mediated anti-viral response, even in mammalian cells (Tuschl, Nature, 411, 494-498(2001)). Since then, RNAi has drawn more attention as a technology that can be applied to differentiated mammalian cells such as human cells.

When RNAi is used to suppress the expression of the midkine gene, siRNAs may be used in place of dsRNA. The term "siRNA" refers to a short double-stranded RNA whose length falls within the non-cytotoxic range. The length of siRNA is not limited to the 21-23 base pairs reported by Tuschl et al. (supra). The siRNA length is not specifically limited as long as it falls within the non-toxic range and can be, for example, 15-49 base pairs, preferably 15-35 base pairs, more preferably 21-30 base pairs. Alternatively, when the siRNA to be expressed is transcribed, the final double-stranded RNA portion can have a length of, for example, 15-49 base pairs, preferably 15-35 base pairs, and more preferably 21-30 base pairs.

For the DNAs of the present invention, constructs that can be used comprise an appropriate sequence (preferably an intron sequence) inserted between the inverted repeats of a target sequence, and are transcribed into double-stranded RNAs having a hairpin structure (self-complementary 'hairpin' RNA (hpRNA)) (Smith, N. A. et al. Nature, 407:319, 2000, Wesley, S. V. et al. Plant J. 27:581, 2001, Piccin, A. et al. Nucleic Acids Res. 29:E55, 2001).

The DNAs for use in RNAi need not be completely identical to the target gene, but have a sequence identity of at least 70% or higher, preferably 80% or higher, more preferably 90% or higher, most preferably 95% or higher (for example, 96%, 97%, 98%, 99% or higher). The nucleotide sequence identity can be determined using the BLAST algorithm designed by Karlin and Altschul (Karlin S, Altschul S F, Proc. Natl. Acad. Sci. USA, 87: 2264-2268 (1990); Karlin S, Altschul S F, Proc. Natl. Acad Sci. USA, 90: 5873-5877 (1993)). A BLAST algorithm-based program called BLASTN has been developed (Altschul S F, et al., J. Mol. Biol., 215: 403 (1990)). Nucleotide sequences are analyzed using BLASTN with the following parameters: for example, score=100 and wordlength=12. When the BLAST and Gapped BLAST programs are used, the default parameters for the programs may be used. Specific procedures for these analysis methods are known.

The double-stranded RNA portion formed via RNA-RNA paring in dsRNA is not limited to completely paired RNAs, but also includes RNAs comprising unpaired portions such as mismatches (the corresponding nucleotides are not complementary) and bulges (one strand has no corresponding nucleotides). In the present invention, the double-stranded RNA portion formed via RNA-RNA paring in dsRNA may comprise both bulges and mismatches. Furthermore, micro RNAs and DNAs encoding them can be used to suppress midkine gene expression.

Compounds which suppress midkine function include, for example, antibodies that bind to midkine.

Anti-midkine antibodies which suppress midkine activity can be similarly prepared by a previously developed method (Muramatsu, H. et al., Dev. Biol. 159, 392-402, 1993). In addition, monoclonal antibodies against human midkine are also available (Unexamined Published Japanese Patent Application No. (JP-A) 2002-085058). However, the antibodies of the present invention are not limited to these antibodies. Anti-midkine antibodies are described in more detail below.

Anti-midkine antibodies for use in the present study may be polyclonal or monoclonal antibodies prepared by generally known techniques. The monoclonal antibodies can be prepared according to known methods. For example, human midkine cDNA has been cloned and has been cloned previously its DNA sequence and the amino acid sequence encoded by the DNA have been reported. The monoclonal antibodies can be prepared against the whole midkine protein antigen, or a portion thereof. Antibodies prepared using a soluble human midkine protein as antigen are particularly preferred. In the present study, the antibodies also include antigen-binding fragments, for example, $F(ab')_2$ and Fab' fragments.

Basically, monoclonal antibody-producing hybridomas can be prepared according to the method of Kohler and Milstein (Kohler, G. & C. Milstein, Nature 256: 495-497, 1975) described below. Specifically, immunization is carried out according to a conventional method using the midkine protein as sensitizing antigen. The resulting immune cells are fused with known parental cells by a conventional cell fusion method. Fused cells are screened for monoclonal antibody-producing cells by a conventional screening method.

To obtain a midkine protein which is used as sensitizing antigen in antibody preparation, for example, in the case of human midkine, the midkine amino acid sequence of JP-A Hei 9-95454 can be used.

As long as the midkine can be used as an antigen to prepare antibodies for use in the present invention, the number of amino acid residues is not limited. The midkine gene sequence is inserted into a known expression vector, and an appropriate host cell is transformed with the resulting construct. Then, the midkine protein of interest is purified from the host cell or culture supernatant using known methods. The resulting purified midkine protein can be used as the sensitizing antigen. Mammals to be immunized with the antigensensitizing antigen are not limited, but are preferably selected by taking into consideration their compatibility with the parental cell used in cell fusion. Typically used are rodents, for example, mice, rats, and hamsters.

Immunization of animals with the sensitizing antigen is carried out according to known methods. For example, the antigensensitizing antigen is typically injected into mammals intraperitoneally or subcutaneously. Specifically, the antigensensitizing antigen is appropriately diluted and suspended in PBS, physiological saline, or such. If required, the diluted antigen is combined with an appropriate amount of a standard adjuvant, for example, Freund's complete adjuvant. After emulsification, the antigen is administered several times to mammals at 14-21 day intervals. In addition, an appropriate carrier may be used for immunizations with the antigensensitizing antigen. After confirming an increase in the desired antibody level in the serum of the mammal thus immunized, immune cells are isolated from the mammal and used in cell fusion. The particularly preferred immune cells are spleen cells.

Preferred mammalian myeloma cells to be fused as the parental cell with the immune cells described above include various known cell lines, for example, P3 (P3×63Ag8.653) (Kearny, J. F. et al., J. Immunol, 123: 1548-1550, 1979), P3×63Ag8U.1 (Yelton, D. E. et al., Current Topics in Microbiology 81: 1-7, 1978), Ns-1 (Kohler, G. & Milstein, C., Eur. J. Immunol., 6: 511-519,1976), SP2/0 (Shulman, M. et al., Nature, 276: 269-270, 1978), FO (de St. Groth, S. F. & Scheidegger, D., J. Immunol. Methods, 35: 1-21, 1980), S194 (Trowbridge, I. S.: J. Exp. Med., 148: 313-323, 1978), and R210 (Galre, G. et al., Nature, 277: 131-133, 1979).

Cell fusion between the immune cells and myeloma cells described above can be essentially achieved by a known method, for example, the method of Milstein et al. (Galfre, G. & Milstein, C. Methods Enzymol. 73: 3-46, 1981). Specifically, the cell fusion described above can be performed, for example, in a standard culture medium in the presence of a cell fusion-promoting agent. Such fusion-promoting agents include, for example, polyethylene glycol (PEG) and the Sendai virus. Furthermore, an auxiliary substance such as dimethylsulfoxide may be added to enhance the fusion efficiency.

The immune cell and the myeloma cell are preferably used in a ratio of, for example, 1:1 to 10:1. Culture media for use in the cell fusion include, for example, media that are suitable for myeloma cell lines, such as RPMI1640 and MEM; and standard culture media that are commonly used for cell culturing. Serum supplements such as fetal calf serum (FCS) can also be used in combination.

In the cell fusion, fused cells (hybridomas) of interest are formed by mixing well predetermined quantities of immune cells and myeloma cells in the culture medium described above, and adding and mixing a PEG solution (average molecular weight from about 1000 to 6000, for example) pre-warmed to about 37° C. at a concentration of 30-60% (w/v). Subsequently, cell fusion-promoting agents and such which are unfavorable to hybridoma growth can be removed by repeatedly adding an appropriate culture medium, centrifuging, and discarding the supernatant.

The hybridomas can be selected by culturing the cells in a standard selection culture medium, for example, HAT medium. The culture is continued in HAT medium for a period of time, typically a few days to several weeks, to ensure the death of cells other than the hybridomas of interest (non-fused cells). Cells are then screened for antibody producing-hybridomas of interest and single-clone isolation is achieved by the standard limiting dilution method.

Furthermore, recombinant antibodies and modified antibodies can be used in the present invention. Recombinant antibodies can be produced as monoclonal antibodies by gene recombination techniques, for example, by cloning antibody genes from hybridomas, inserting the genes into appropriate vectors, and introducing the vectors into hosts (see, for example, Borrebaeck, C. A. K. & Larrick, J. W., THERAPEUTIC MONOCLONAL ANTIBODIES, Published in the United Kingdom MACMILLAN PUBLISHERS LTD, 1990). Modified antibodies include, for example, chimeric antibodies and humanized antibodies. Chimeric antibodies can be produced by ligating a DNA encoding the V region of a non-human antibody and a DNA encoding the C region of a human antibody, inserting the ligate into an expression vector, and introducing the resulting construct into hosts (EP 125023, PCT WO96/02576).

Antibodies used in the present invention can be an antibody fragment or a modified antibody, as long as it binds to midkine and inhibits midkine activity. Such antibody fragments include, for example, Fab, F(ab')2, Fv, and single-chain Fv(scFv) produced by connecting the Fvs of the H and L chains with an appropriate linker.

Compounds other than the antibodies can also be used to prevent post-laparotomy adhesions according to the present invention, as long as they suppress midkine activity. Such compounds can be identified by contacting a test compound with midkine, determining the midkine activity in the presence of the test compound, and then selecting a compound that significantly reduces midkine activity compared to the activity in the absence of the test compound. The test compounds of the present invention include, without being limited thereto, cell extracts, purified proteins or peptides, artificially synthesized low-molecular-weight compounds, etc. The test compounds may be compounds that inhibit the binding between midkine and midkine receptors. Various activities of midkine are known. For example, the migration of neutrophils and macrophages is disclosed in Muramatsu, T., J. Biochem., 132, 359-371, 2002;Kadomatsu, K. et al., Biochem. Biophys. Res. Commun. 151, 1312-1318 1988; Horiba, M. et al., J. Clin. Invest. 105, 489-495, 2000;Takada, T. et al., J. Biochem. 122, 453-458, 1997;Sato, W., et al., J. Immunol. 167, 3463-3469 2001. Candidate compounds which suppress midkine activity can be identified using the midkine-binding activity as an index. Specifically, candidate compounds which suppress midkine activity can be obtained by contacting a test compound with midkine, determining the midkine-binding activity of the test compound, and selecting a compound that exhibits a significant binding activity.

A compound suppressing midkine gene expression or midkine protein function can be formulated and administered as a pharmaceutical preparation by known pharmaceutical production methods. For example, the compound can be administered in a dosage form suitable for effective administration to the living body, in combination with an appropriate carrier or vehicle commonly used for pharmaceutical agents, for example, sterilized water, physiological saline, a vegetable oil (for example, sesame oil or olive oil), a coloring agent, an emulsifier (for example, cholesterol), a suspending agent (for example, gum Arabic), a surfactant (for example, poly(oxyethylene) hydrogenated castor oil surfactant), a solubilizing agent (for example, sodium phosphate), a stabilizing agent (for example, sugar, sugar alcohol, and albumin), or a preservative (paraben).

BEST MODE FOR CARRYING OUT THE INVENTION

Herein below, the present invention will be specifically described using Examples, however, it is not to be construed as being limited thereto.

EXAMPLE 1

Effects of Midkine on Post-Laparotomy Adhesions (1) Preparation Of Knockout Mice Midkine (−/−) mice were created as described (Nakamura, E. et al., Genes Cells, 3, 811-822, 1998). The heterozygote was backcrossed to C57BL/6J mice for nine generations. Then, the backcrossed progenies were crossed with each other to produce midkine (−/−) mice having the C57BL/6J genetic background. C57BL/6J mice were used as the wild-type control.

(2) Test Example 1

Laparotomy was performed aseptically on 16-week old wild-type mice and midkine gene knockout mice, which had been placed under general anesthesia by intraperitoneal injection of Ketalar (1 mg/kg). A 5×5 mm excision was made in the the peritoneum at the inside of the abdominal wall of the left epigastric region. After the bleeding was arrested by bipolar electrocoagulation, the abdomen was stitched closed with nylon threads. Seven days later, the abdomen was reopened by the same procedure described above. The ratio of omental adhesion area:experimental injury area (area of omental adhesion ×100/area of experimental injury) was determined using the image analysis software, Scion Image (Scion Corporation).

Figure 1:
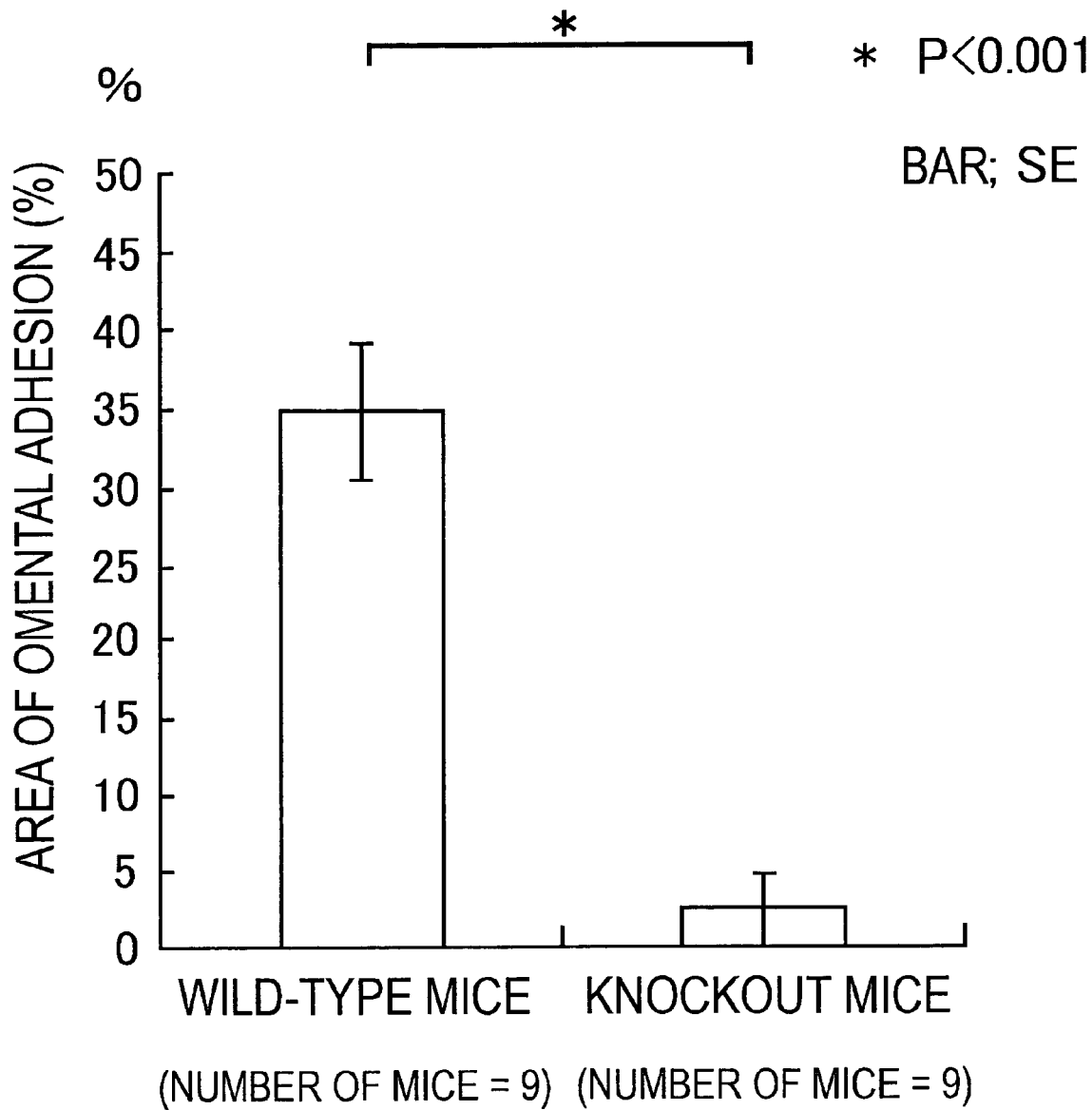
FIG. 1 is a graph showing the average values of the area ratio of omental adhesion area:experimental injury area produced in wild-type mice and midkine gene-knockout mice. The values were calculated using the formula: [percentage of omental adhesion area (%)=area of omental adhesion ×100/area of experimental injury]. Significant difference test was performed on two unpaired groups.

The values were 34.6% for the wild-type mice and significantly lower (2.33%) for the knockout mice (FIG. 1).

(3) Test Example 2

Four-month old female mice were anesthetized with 40 mg/kg of sodium pentobarbital (Abbott Laboratories, North Chicago, Ill.) by intraperitoneal injection, after which laparotomy was performed. A 5×5 mm abrasion was made on the inside of the left epigastric region using a No. 11 surgical blade. After the bleeding was arrested by bipolar cautery, the abdomen was closed using a 5-0 nylon surgical suture. Seven days later, the abdomen was reopened under sodium pentobarbital anesthesia as described above. The adhesion areas of both the omentum and the injection site were measured using the Scion image analysis software (Scion Corporation; Frederick, Md.). In tests using pumps to deliver midkine, physiological saline containing human midkine (1 mg/ml) or human serum albumin (1 mg/ml; Wako Pure Chemical Industries, Osaka, Japan) was injected into midkine (−/−) mice using an osmotic pump (Alza Corporation; Palo Alto, Calif.). The pump implanted subcutaneously on the back delivered a total of 90 μl solution over seven days. The human midkine produced in yeast was a generous gift from Dr. Sakuma of Cell Signals Inc. In the case of partial hepatectomy, mice were anesthetized with a pentobarbital dose of 40 mg/kg of body weight. The right lobe, left lobe, and middle lobe, as well as the left lateral lobe were excised surgically. The resulting adhesions were observed two weeks later.

Figure 2:
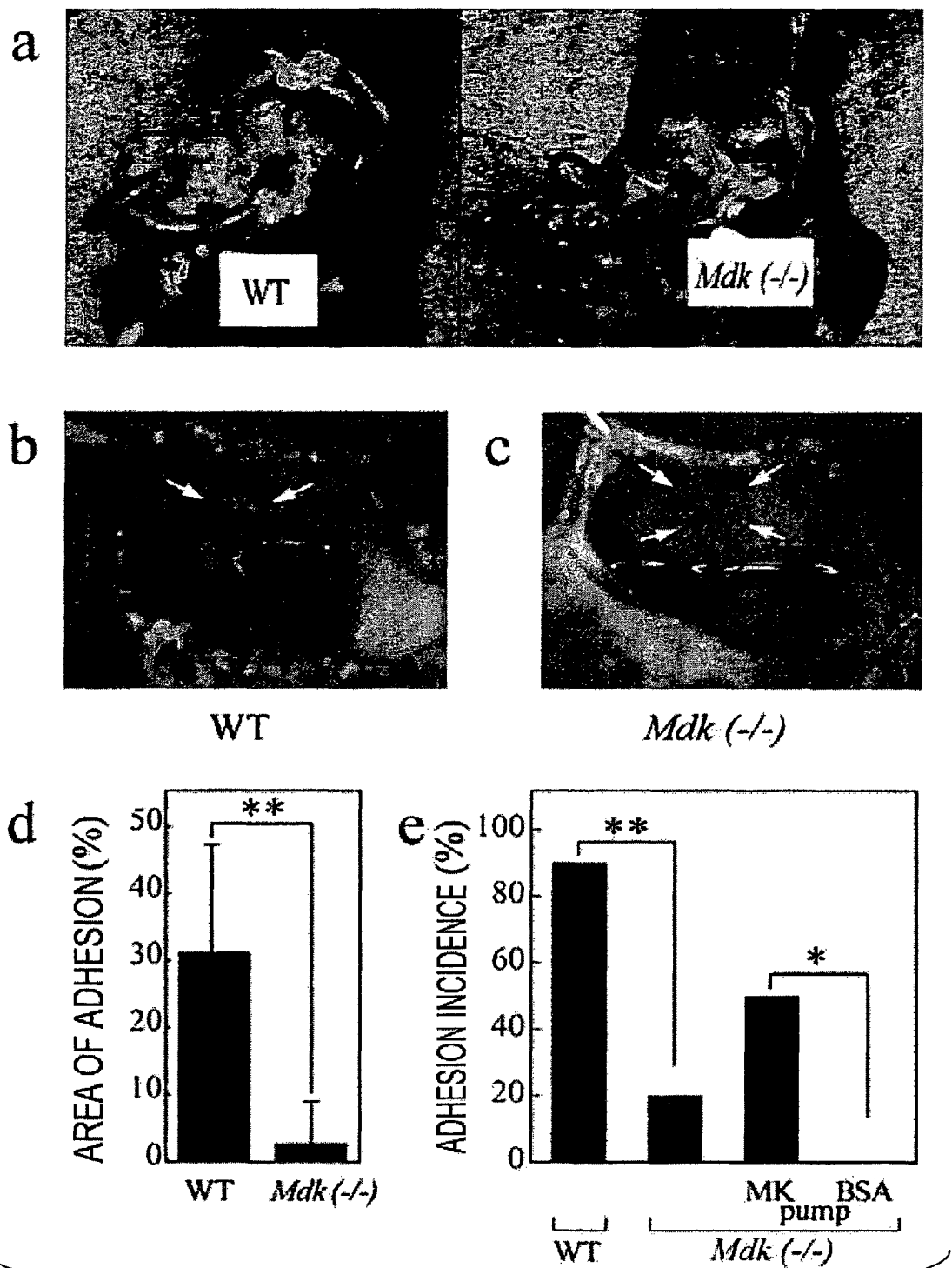
FIG. 2: photographs (a-c) and diagrams (d and e) illustrating the reduction of intraperitoneal adhesions in midkine (−/−) mice. a: intestinal adhesions recognized two weeks after partial hepatectomy. Representative cases of WT mice (n=10) and midkine (−/−) mice (n=10) are shown. b and c: adhesion of the omentum to the injured peritoneal walls. The areas indicated by arrows were surgically detached, and the adhesions were examined seven days later. Representative examples of the WT mice (b) and the midkine (−/−) mice (c) are shown. d and e: quantitative estimates of the reduction of omental adhesions in the injured peritoneal walls. d: area of adhesion expressed as a percentage of the defective area in the WT mice (n=10) and the midkine (−/−) mice (n=10). e: the incidence rate of adhesion in the WT and the midkine (−/−) mice which were either untreated (n=10), or injected with midkine (n=10) or bovine serum albumin (BSA) (n=10). *$p<0.05$;**$p<0.01$. The statistical significance was evaluated by using the Student t-test in d, and the Fisher's exact test in e.

The present inventors found that the intestinal adhesion after partial hepatectomy was less severe in the midkine (−/−) mice than in the wild-type (WT) mice (FIG. 2a). While adhesions occurred in all the WT mice, they were not observed in nearly 50% of the midkine (−/−) mice. The present inventors then developed an omental adhesion assay for more detailed analyses. An injury was produced in the peritoneal walls of the midkine (−/−) or WT mice. Seven days after the injury, omental adhesions to the peritoneal wall were observed in the WT mice (FIG. 2b); in contrast, few or no adhesions occurred in the midkine (−/−) mice (FIG. 2c). Average values for the area of omental adhesion (FIG. 2d) and the incidence rate of adhesion (FIG. 2e) were significantly lower in the midkine (−/−) mice than in the WT mice. The adhesion formation in these midkine (−/−) mice resumed significantly upon subcutaneous administration of midkine via osmotic pumps. The administration of bovine serum albumin produced no effect (FIG. 2e). This finding confirmed the correlation of the loss of midkine with the decreased adhesion in the midkine (−/−) mice. From the results described above, the present inventors concluded that midkine plays a fundamental role in intraperitoneal adhesion.

EXAMPLE 2

Midkine Expression in Regions of Adhesion

Midkine expression was determined by Western blotting of the heparin-binding protein derived from 1.7 mg of extract as described (Muramatsu, H. et al., Dev. Biol. 159, 392-402, 1993). The anti-mouse midkine antibody was produced as previously described (Muramatsu, H. et al., Dev. Biol. 159, 392-402, 1993). The sites of midkine expression were revealed by immunohistochemistry (Nakamura, E. et al., Genes Cells, 3, 811-822, 1998) using an affinity-purified rabbit anti-mouse midkine antibody as the primary antibody and a horseradish peroxidase-conjugated affinity-purified goat anti-rabbit IgG (Jackson ImmunoResearch Laboratories, Inc.; West Grove, Pa.) as the secondary antibody. Positive signals were visualized using diaminobenzidine tetrahydrochloride (Amersham Pharmacia Biotech; Tokyo, Japan). A fluorescein isothiocyanate-labeled goat anti-rabbit IgG (Sigma; St. Louis, Mo.) can also be used as the secondary antibody. Staining of the macrophage marker or the neutrophil marker was carried out by the same method described above. The sections were stained with a rat monoclonal antibody against the mouse monocyte-macrophage marker F4/80 (Serotec Ltd.; Oxford, England) or a rat monoclonal antibody against the mouse neutrophil marker 7/4 (Serotec Ltd.), followed by incubation with a horseradish peroxidase-conjugated goat anti-rat IgG (Jackson ImmunoResearch Laboratories, Inc.). Cell numbers in the optical fields were counted under 400-fold magnification. The average values were obtained from a total of 12 optical fields. Four WT mice and four midkine (−/−) mice were examined to determine the average values and SDs at various time points. Intraperitoneal macrophages were isolated from the mice by the same procedure described previously (Xie, B., et al., J. Immunol. 152, 3637-3644, 1994).

Figure 3:
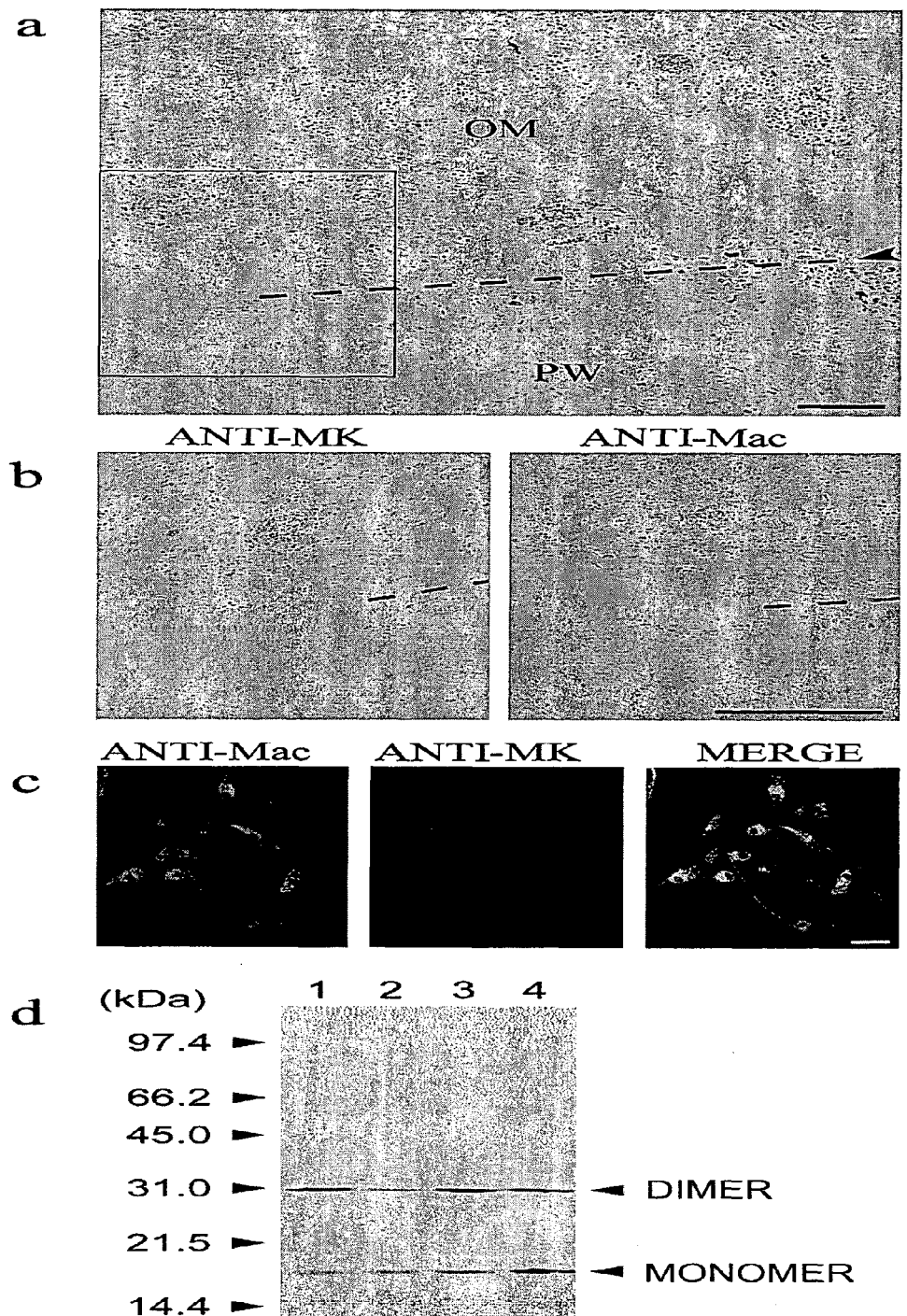
FIG. 3: photographs (a-c) and a diagram (d) showing the localization of midkine in the the omentum. a: immunostaining of the adhesion area using an anti-midkine antibody on day 5. The broken line indicates the site of adhesion. OM: omentum; PW: peritoneal wall. Scale bar represents 100 μm. b: enlargement of the rectangular area in a. Anti-midkine: staining with an anti-midkine antibody; anti-Mac: staining with an anti-monocyte-macrophage marker antibody. Scale bar indicates 100 μm. c: staining of intraperitoneal macrophages using an anti-macrophage marker antibody and an anti-midkine antibody. Scale bar represents 50 μm. d: identification of midkine in the omentum using Western blotting. Lanes 1, 2, 3 and 4 show samples collected on days 0, 3, 5 and 7, respectively.

Midkine is mainly expressed at embryonic stages and is present only in restricted sites of adult tissues; its expression is often increased after various injuries (Horiba, M. et al., J. Clin. Invest. 105, 489-495, 2000;Sato, W., et al., J. Immunol. 167, 3463-3469 2001;Kadomatsu, K. et al., J. Cell Biol. 110, 607-616, 1990;Mitsiadis, T. A. et al., Development 121, 37-51, 1995; Yoshida, Y. et al., Dev. Brain Res. 85, 25-30, 1995). During the process of adhesion, midkine is expressed mainly in the omentum. An example of the immunohistochemical stain is shown in FIG. 2a. Midkine was found mainly in the macrophage-like cells and blood vessels. Midkine expression in the macrophages was confirmed by double-staining with an anti-midkine antibody and an anti-macrophage marker antibody (FIG. 3b), as well as by midkine expression analysis of isolated intraperitoneal macrophages (FIG. 3c). The Western blot analysis showed that the omental midkine was present as a monomer or a dimer, and its molecular weight was 30 kDa (FIG. 3d).

Figure 4:
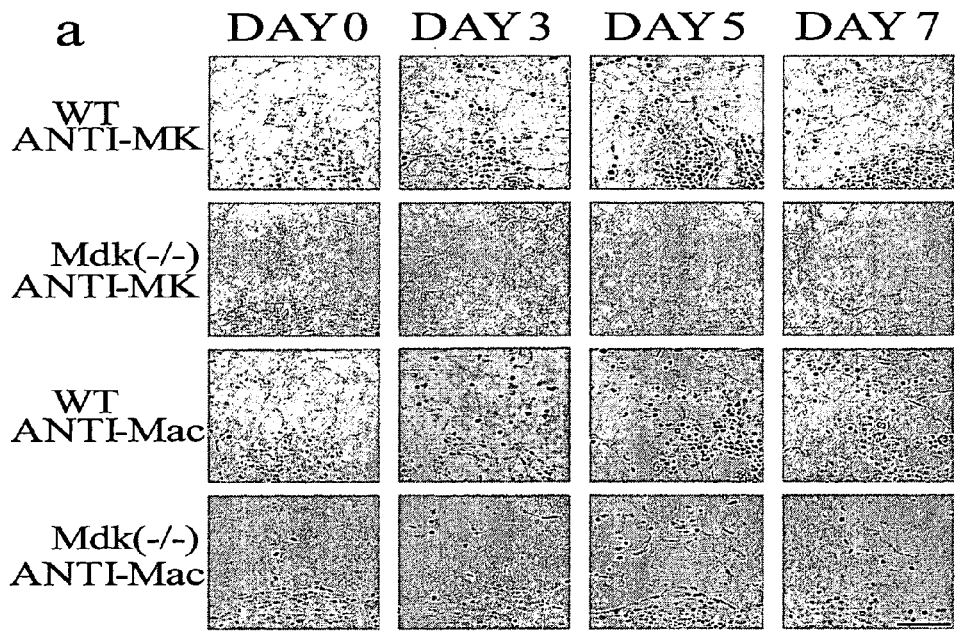
FIG. 4: photograph (a) and diagrams (b-e) showing the reduction of inflammatory leukocyte migration in midkine (−/−) mice. a: immunohistochemical staining of omental sections on different days after the injury. Scale bar represents 50 μm. b-e: the number of macrophages (b and c) and neutrophils (d and e) in the omentum (b and d) and in the injured peritoneal walls (c and e). Closed bar: WT; open bar: midkine (−/−). *$p<0.05$;**$p<0.01$. The statistical significance was evaluated by using Student t-test.
Figure 4:
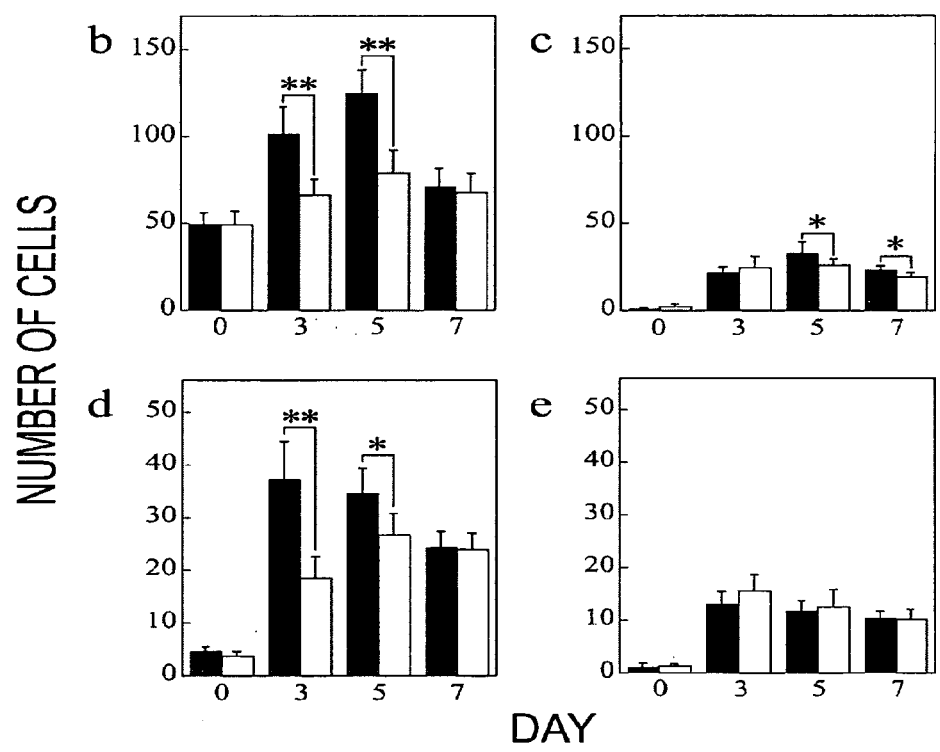

The present inventors revealed that the number of macrophages in the omentum around the adhesion sites reached its peak on day 3 and day 5 following the injury, and cells were recruited to these sites during adhesion formation (FIG. 4a). One of the macrophage sources is omental milky spots (Mandache. E. et al., Morphol. Embryol. (Bucur) 31, 137-142 1985). Macrophage migration was more prominent in the WT mice than in the midkine (−/−) mice. These findings were confirmed by quantitative evaluations (FIG. 4b). The present inventors reached the same conclusion regarding the migration of neutrophils to the omentum (FIG. 4d). Only subtle differences in the migration of leukocytes to the injured peritoneal walls were observed between the WT and the midkine (−/−) mice (FIGS. 4c and 4e).

Industrial Applicability

Midkine directly and or indirectly enhances the migration of neutrophils and macrophages via chemokine induction (Horiba, M. et al., J. Clin. Invest. 105, 489-495, 2000; Takada, T. et al., J. Biochem. 122, 453-458, 1997;Sato, W., et al., J. Immunol. 167, 3463-3469, 2001). When compared to wild-type mice, neointima formation after ischemic injury (Horiba, M. et al., J. Clin. Invest. 105, 489-495, 2000) and nephritis (Sato, W., et al., J. Immunol. 167, 3463-3469 2001) are significantly suppressed in midkine (−/−) mice, and this is accompanied by a reduced recruitment of inflammatory leukocytes in midkine (−/−) mice. The present inventors believe that the series of events described below take place during adhesion formation. An injured peritoneal wall induces infiltration of leukocytes by secreting factors that activate the omentum. The recruitment of inflammatory leukocytes to the omentum is enhanced by midkine, which is present in blood vessels and is also secreted by macrophages. Midkine in macrophages can also participate in the activation. After macrophage recruitment, midkine secreted by the macrophages may further accelerate the leukocyte recruitment. It is possible that the recruited leukocytes secrete factors that enhance the adhesion activity of the omentum. However, the possibility that midkine also directly stimulates the omentum could not be ruled out completely. The present inventors believe that intraperitoneal macrophages play a major role in the formation of adhesions between organs, by enhancing the migration and/or activation of macrophages. In this regard, it should be pointed out that the omental milky spots might serve as a major source of intraperitoneal macrophages.

The finding that midkine is an important factor in intraperitoneal adhesion formation offers fresh insight intomechanisms underlying the adhesion formation process and methods for preventing adhesions. In particular, therapeutic strategies for inhibiting midkine activity or biosynthesis can be useful for adhesion prevention. Recently, absorbable films have been introduced into and kept in the abdominal cavity to prevent intraperitoneal adhesions (Beck, D. E. Eur. J. Surg.

Suppl. 577, 49-55 1997). However, this technique is effective only in organs separated by the membrane. Thus, other effective means are urgently needed to prevent intraperitoneal adhesions. Various experiments have been carried out to prevent such adhesions (Vrijland, W. W. et al., Ann. Surg. 235, 193-199, 2002;Gimbel. M. L. et al., Arch. Surg. 136, 311-317, 2001;Cervantes-Sanchez, C. R. et al., J. Surg. Res. 110, 207-210, 2003;Nagler, A. et al., Am. J. Obstet. Gynecol. 180, 558-563, 1999). Midkine is mainly expressed in mid-gestation embryos, and its expression in adult tissues is restricted (Kadomatsu, K. et al., J. Cell Biol. 110, 607-616 1990, Mitsiadis, T. A. et al., Development 121, 37-51 1995). Because of its expression pattern, midkine has hardly any side effects and is thus a preferred potential target. Anti-midkine antibodies and antisense oligo DNAs against midkine have already been developed and revealed to be effective to inhibit the midkine-dependent growth of tumor cells (Muramatsu, H. et al., Dev. Biol. 159, 392-402, 1993;Takei, Y. et al., Cancer Res., 61 8486-8491, 2001).

The invention claimed is:

1. A method of preventing post-laparotomy adhesions in a laparotomy subject by administering to said subject a compound which suppresses midkine protein function, which compound is a midkine-binding antibody or antigen-binding fragment thereof.

2. The method of claim 1 wherein the antibody is immunoreactive with human midkine.

3. The method of claim 1 wherein the antibody is monoclonal.

4. The method of claim 3 wherein the antibody is humanized.

5. The method of claim 3 wherein the antibody is chimeric.

6. The method of claim 3 wherein the antibody is single chain.

7. The method of claim 1 wherein the antibody fragment is an Fab or F(ab')$_2$ fragment.

* * * * *